United States Patent [19]

Meyers

[11] Patent Number: 5,324,292
[45] Date of Patent: Jun. 28, 1994

[54] FRACTURE FIXATION ASSEMBLY WITH SELECTIVELY REMOVABLE PROTRUSION

[75] Inventor: John E. Meyers, Columbia City, Ind.

[73] Assignee: Zimmer, Inc., Warsaw, Ind.

[21] Appl. No.: 15,748

[22] Filed: Feb. 10, 1993

[51] Int. Cl.⁵ .............................. A61F 5/04; A61F 2/32
[52] U.S. Cl. ......................................... 606/73; 606/62; 606/66; 606/67
[58] Field of Search .......................... 606/60, 62, 64, 65, 606/66, 67, 72, 73; 623/23

[56] References Cited

U.S. PATENT DOCUMENTS

| | | | |
|---|---|---|---|
| 2,702,543 | 2/1955 | Pugh et al. | 606/65 |
| 2,834,342 | 5/1958 | Yost | 606/67 |
| 3,489,143 | 1/1970 | Halloran | 606/67 |
| 4,095,591 | 6/1978 | Graham, Jr. et al. | |
| 4,172,452 | 10/1979 | Forte et al. | 606/67 |
| 4,432,358 | 2/1984 | Fixel. | |
| 4,530,355 | 7/1985 | Griggs. | |
| 4,612,920 | 9/1986 | Lower. | |
| 4,657,001 | 4/1987 | Fixel. | |
| 4,759,352 | 7/1988 | Lozier. | |

OTHER PUBLICATIONS

Key-Free TM Compression Hip Screw–Zimmer–1978.

Primary Examiner—Stephen C. Pellegrino
Assistant Examiner—Sonya Harris
Attorney, Agent, or Firm—Margaret L. Geringer

[57] ABSTRACT

A fracture fixation system comprising an elongated inner member 20 and a hollow barrel 14 adapted to receive the inner member 20. The barrel 14 includes an integral protrusion portion 15 for mating with a corresponding recess 24 on the inner member 20. The protrusion portion 15 is selectively removable by separation from the barrel 14, so that if the protrusion 15 is not removed, the protrusion 15 and corresponding recess 24 prevent rotation between the barrel 14 and the inner member 20, or alternatively, if the protrusion 15 is removed, this allows rotation between the inner member 20 and the barrel 14.

12 Claims, 3 Drawing Sheets

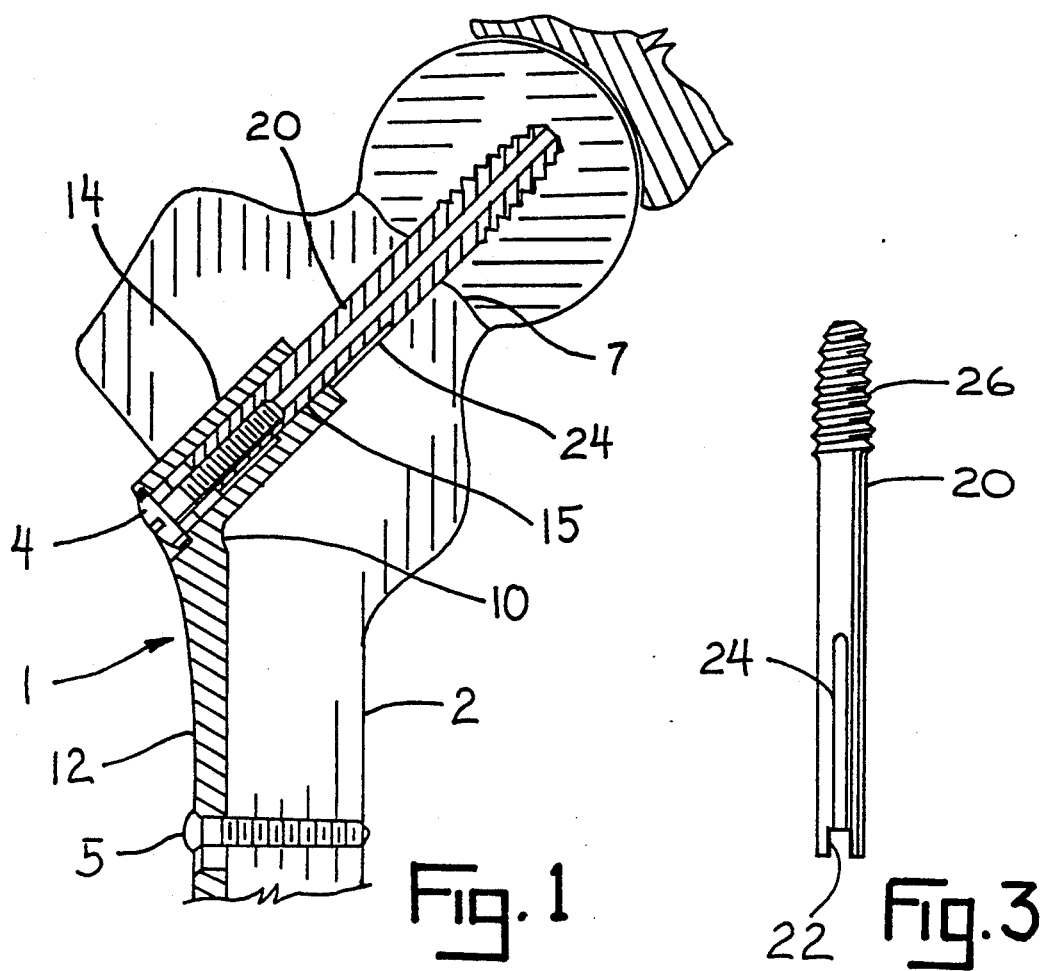
Fig. 1
Fig. 3
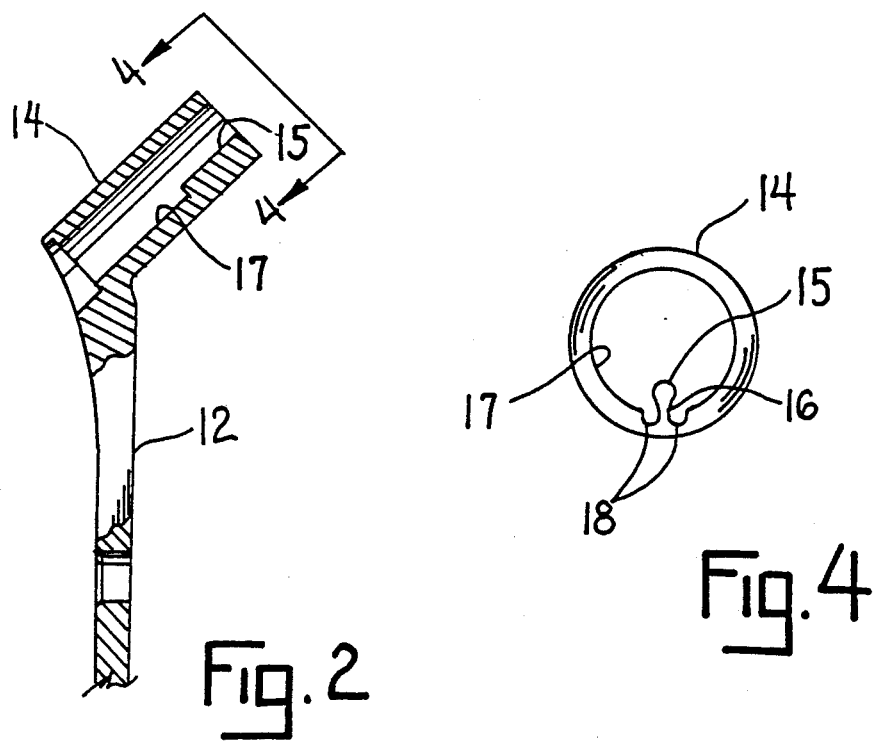
Fig. 2
Fig. 4

FRACTURE FIXATION ASSEMBLY WITH SELECTIVELY REMOVABLE PROTRUSION

FIELD OF THE INVENTION

This invention relates to the field of orthopaedic fracture fixation devices. In particular, this invention relates to such fracture fixation devices which include tubular members which receive another component therein. While this invention is particularly suitable for compression hip screw devices, the features of this invention could be adapted, as appropriate, to other fracture fixation devices, such as supracondylar tube/plate devices, intramedullary nails with interlocking screws or lag screws, or other suitable devices.

BACKGROUND OF THE INVENTION

In the field of orthopaedics, it is well known to utilize various compression hip screw devices. Typically, a compression hip screw includes a lag screw with a tube or hollow barrel disposed over the lag screw and a compression screw threadably coupled to the lag screw. The barrel and the lag screw extend into the bone with the lag screw extending across the fracture. A bone plate typically extends from the barrel for attachment to the bone with bone screws. The compression screw permits application of a compressive force between the plate and the lag screw.

It is known to provide compression hip screws which include an intergaging key between the lag screw and the barrel to prevent rotation therebetween. Such keyed devices are shown in U.S. Pat. No. 2,702,543 to Pugh et al. and U.S. Pat. No. 4,095,591 to Graham, Jr. et al. Other such devices are provided without any keyed portion between the lag screw and barrel which allows rotation therebetween and thus does not require the alignment necessary with keyed devices. An example of such a device is the KEY-FREE TM Compression Hip Screw which was sold by Zimmer, Inc. of Warsaw, Ind.

Various compression hip screw assemblies provide for a separately insertable locking member of various configurations as disclosed by the following: U.S. Pat. Nos. 4,432,358 and 4,657,001 to Fixel; U.S. Pat. No. 4,530,355 to Griggs; U.S. Pat. No. 4,612,920 to Lower; and U.S. Pat. No. 4,759,352 to Lozier. In Griggs and Lower and Lozier, the separately insertable locking member may optionally be used if a keyed device is desired, or selectively not inserted if a keyless device is desired. Whether or not a keyed or keyless system is utilized typically depends upon the preference of the surgeon. While these devices provide the option for a keyed or keyless device, the separately insertable locking member or key can be inconvenient to line up and insert during a surgical procedure if a keyed device is desired by the surgeon.

SUMMARY OF THE INVENTION

The present invention provides the option of a keyed or keyless device, but alleviates the inconvenience of a separately insertable locking member. This invention provides a fracture fixation system for fixation Of d fractured bone comprising an elongated inner member and a hollow barrel adapted to receive the inner member. The barrel includes an integral protrusion portion extending from an inner tubular surface of the barrel, and the inner member includes a corresponding recess for receiving the protrusion portion therein to prevent rotation between the inner member and the barrel. The protrusion portion is selectively removable by separation from the barrel in order to allow rotation of the inner member with respect to the barrel, if desired.

The protrusion portion may include a reduced or narrowed-down portion adjacent the barrel, so that the protrusion portion is adapted to break along the reduced portion. A removal tool is provided to selectively remove the protrusion portion.

Accordingly, it is an advantage of the invention to provide a novel fracture fixation system which provides the capability for both a keyed or keyless system between mating components.

Another advantage of the invention is to provide a simple, convenient system for providing such a keyed or keyless system.

A further advantage of the invention is to provide such a keyed or keyless system which eliminates the need for a separately insertable locking member in order to provide the keyed portion of the system.

Still other advantages of the invention will become apparent upon reference to the accompanying drawings.

BRIEF DESCRIPTION OF THE DRAWINGS

FIG. 1 depicts a compression hip screw assembly in accordance with the present invention with the assembly shown in cross-section as applied to a femur having a fracture at a neck thereof.

FIG. 2 is a partial cross-sectional view of the tube/plate of the assembly of FIG. 1.

FIG. 3 is a side view of the lag screw of the assembly of FIG. 1.

FIG. 4 is an end view of the tube/plate taken along lines 4—4 of FIG. 2.

DESCRIPTION OF THE PREFERRED EMBODIMENT

Figure 5:
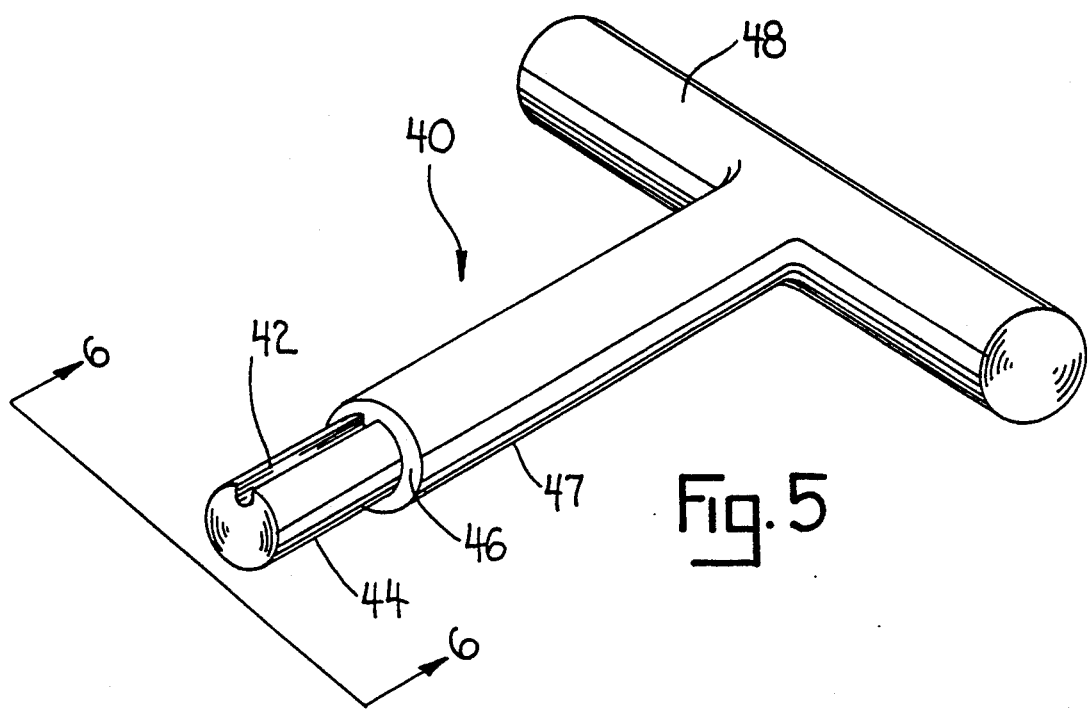
FIG. 5 is a perspective view of the removal tool.
Figure 6:
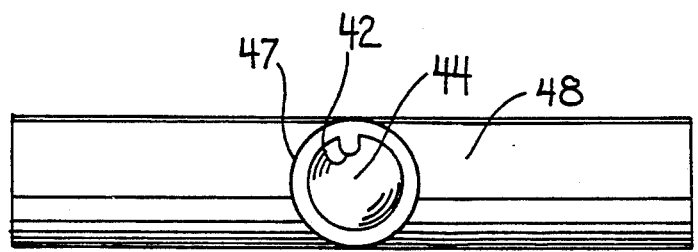
FIG. 6 is an end view of the removal tool token along lines 6—6 of FIG. 5.
Figure 7:
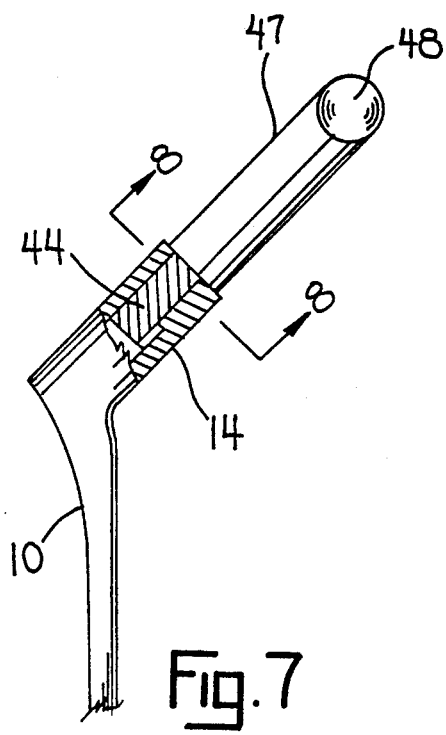
FIG. 7 is a partial cross-sectional view of the tube/plate with the removal tool inserted into the barrel of the tube/plate.

The preferred embodiment described herein is not intended to be exhaustive or to limit the invention to the precise form disclosed. Rather, it is chosen and described to best explain the invention so that others skilled in the art might utilize its teachings.

Accordingly, FIGS. 1-9 illustrate the preferred embodiment of a fracture fixation system in accordance with the present invention. The invention will be described with reference to a compression hip screw assembly 1. However, it is understood that the invention is not limited thereto and that the features of the invention could be adapted to other fracture fixation assemblies.

The compression hip screw assembly 1, as shown in FIG. 1, is applied to a femur 2 to which is fractured at 7. The assembly 1 includes a lag screw or inner member 20 with a tube/plate member 10 assembled thereto. The tube/plate 10 includes a hollow barrel 14 disposed over the lag screw 20 and a bone plate portion 12 extending from barrel 14. The bone plate 12 is secured to the femur with bone screws, such as 5. A compression screw 4 is threadably coupled to lag screw 20 in order to apply a compressive force between the tube/plate 10 and lag screw 20. Lag screw 20 includes threads 26 at one end and a slot 22 at the other end, so that a screwdriver (not shown) can be utilized to advance lag screw 20 into femur 2.

Figure 10:
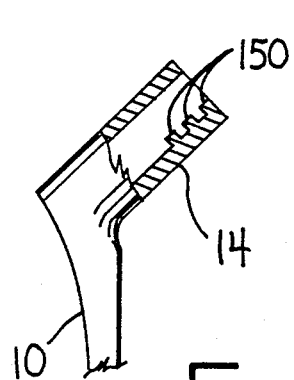
FIG. 10 is a partial cross-sectional view of the tube/plate of the assembly illustrating an alternate embodiment of the protrusion portion.
Figure 8:
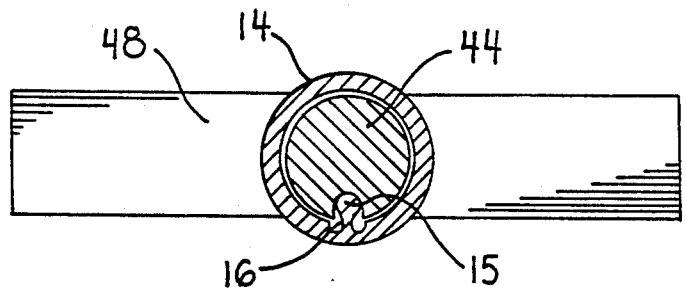
FIG. 8 is a cross-sectional view taken along lines 8—8 of FIG. 7.

The barrel 14 includes an integral protrusion portion 15 extending from an inner tubular surface 17 of barrel 14. The protrusion portion 15 may be single elongated rib, such as shown in FIG. 2 or a plurality of extending portions 150, such as shown in FIG. 10. The inner member or lag screw 20 includes a corresponding recess 24 which may be an elongated recess 24, as shown in FIG. 3, for receiving the rib 15. When the rib 15 and recess 24 are assembled as shown in FIG. 1, rotation is prevented between the barrel 14 and inner member 20.

Figure 9:
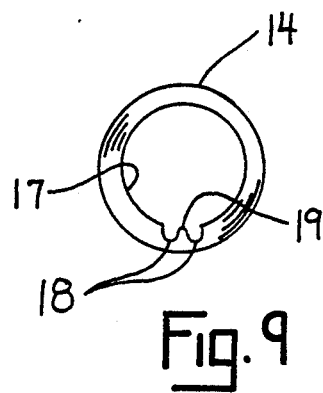
FIG. 9 is an end view of the tube/plate after the protrusion portion has been removed.

The rib 15 on barrel 14 is selectively removable prior to assembly of barrel 14 with inner member 20 by separation of the rib 15 from barrel 14 in order to allow rotation of the inner member with respect to the barrel 14. The rib 15 preferably includes a reduced or narrowed portion 16 adjacent the barrel 14, so that the rib 15 is adapted to break along the reduced portion. The reduced portion 16 also preferably extends below the inner tubular surface 17 of barrel 14, so that the rib 15 will break off below the tubular surface 17 of barrel 14, as shown in FIG. 9. A recessed area 18 is thus formed on either side of the reduced portion 16 facilitating the separation of the rib 15 from barrel 14, if a keyless system is desired.

A removal tool 40, as shown in FIGS. 5–8, is utilized to provide a simple way to remove the protrusion portion or rib 15 from the barrel 14. The tool 40 includes an elongated groove 42 in the elongated cylindrical distal end 44. Groove 44 is adapted to fit about rib 15 in order to selectively apply force thereto in order to remove or break off the rib from the barrel 14. An enlarged extension member 47 may extend from distal end 44 of tool 40, as shown in FIG. 5, which provides a shoulder 46. Shoulder 46 thus abuts against the end of the barrel 14 when tool 40 is fully inserted into barrel 14. A cross bar handle 48 is attached to member 47 to help apply manual force to tool 40 in order to break off rib 15. The rotational force would be applied to the tool 40 in order to break off rib 15 in order to provide a keyless system which will allow rotation between the inner member 20 and barrel 14. Since the rib 15 is broken off at reduced portion 16 below the inner tubular surface 17, the break off surface 19 of rib 15 is below tubular surface 17, and thus does not interfere with the inner member 20 once it is inserted into barrel 14 after rib 15 has been removed. Rotation is thus allowed between inner member 20 and barrel 14.

It is noted that the fixation device and corresponding tool of the present invention may be manufactured by any appropriate manufacturing method. In addition, any suitable materials may be utilized with this system. The implantable portions, such as the tube/plate 10, lag screw 20, compression screw 4, and screws 5 may be made of 22-13-5 stainless steel, or any other suitable implantable material. The portions not implantable, such as tool 40, may be made of stainless steel or any other suitable material. In addition, the device of the present invention may be implanted in accordance with any suitable surgical technique.

While this invention has been described in terms of a particularly advantageous embodiment, those skilled in the art can appreciate that modifications can be made without departing from the spirit and scope of this invention.

I claim:

1. A fracture fixation kit for fixation of a fractured bone comprising an elongated inner member and a hollow barrel adapted to receive the inner member, the barrel including an integral, protrusion means extending from an inner tubular surface of the barrel, and the inner member including a corresponding recess for receiving the protrusion means therein to prevent rotation between the inner member and the barrel, and wherein the system further includes a removal tool and wherein the protrusion means is selectively removable with the removable tool by separation of the protrusion means from the barrel in order to allow rotation of the inner member with respect to the barrel.

2. The kit of claim 1 wherein the protrusion means is an elongated rib.

3. The kit of claim 1 wherein the protrusion means comprises a plurality of extending portions.

4. A fracture fixation kit for fixation of a fractured bone comprising an elongated inner member and a hollow barrel adapted to receive the inner member, the barrel including an integral, protrusion means extending from an inner tubular surface of the barrel, and the inner member including a corresponding recess for receiving the protrusion means therein to prevent rotation between the inner member and the barrel, and wherein the system further includes a removal tool and wherein the protrusion means is selectively removable with the removal tool by separation of the protrusion means from the barrel in order to allow rotation of the inner member with respect to the barrel, and wherein the protrusion means includes a reduced or narrowed-down portion adjacent the barrel, so that the protrusion means is adapted to break along the reduced portion.

5. The kit of claim 4 wherein the removal tool includes a groove which is adapted to fit about the protrusion means in order to selectively apply force thereto in order to remove the protrusion means from the barrel.

6. The kit of claim 4 wherein the reduced portion extends below the inner tubular surface of the barrel, so that the protrusion means is adapted to break off below the tubular surface of the barrel.

7. A screw assembly kit for fixation of a fractured bone comprising an elongated screw, a plate member including a hollow barrel adapted to receive the screw, the barrel including an integral, elongated rib extending from an inner surface of the barrel, and the screw including a corresponding recess for receiving the rib therein to prevent rotation between the screw and the barrel, and wherein the system further includes a removal tool and wherein the elongated rib is selectively removable with the removal tool by separation of the elongated rib from the barrel in order to allow rotation of the screw with the respect to the barrel.

8. The kit of claim 7 wherein the elongated rib includes a reduced or narrowed-down portion adjacent the barrel, so that the elongated rib is adapted to break along the reduced portion.

9. A fracture fixation kit for fixation of a fractured bone comprising an elongated inner member and a hollow barrel adapted to receive the inner member, one of the barrel and the inner member including an integral, protrusion means extending therefrom and the other of the barrel and the inner member including a corresponding recess for receiving the protrusion means therein to prevent rotation between the inner member and the barrel, and wherein the kit further includes a removal tool and wherein the protrusion means is selectively removable with the removal tool in order to allow rotation of the inner member with respect to the barrel.

10. The kit of claim 9 wherein the protrusion means includes a reduced or narrowed-down portion adjacent the barrel, so that the protrusion means is adapted to break along the reduced portion.

11. A method of selectively removing a protrusion means from a fracture fixation device comprising:
  providing a fracture fixation assembly including an elongated inner member and a hollow barrel adapted to receive the inner member, wherein the barrel includes an integral protrusion means extending from an inner tubular surface of the barrel, and wherein the inner member includes a corresponding recess for receiving the protrusion means therein to prevent rotation between the inner member and the barrel;
  providing a removal tool including a groove which is adapted to fit about the protrusion means;
  selectively inserting the tool into the barrel with the groove of the tool about the protrusion means of the barrel;
  selectively applying force to the tool to break off the protrusion means from the barrel;
  assembling the barrel, which has had the protrusion means selectively removed, to the extending member, thus allowing rotation of the inner member with respect to the barrel.

12. The method of claim 9 in which the method further includes providing the protrusion means with a reduced or necked-down portion adjacent the barrel, so that the protrusion means is adapted to break along the reduced portion.

* * * * *